(12) United States Patent
Benneteau et al.

(10) Patent No.: US 6,979,540 B2
(45) Date of Patent: Dec. 27, 2005

(54) METHOD FOR SYNTHESIZING AND IMMOBILIZING NUCLEIC ACIDS ON A SILANIZED SOLID SUPPORT

(75) Inventors: Bernard Benneteau, Talence (FR); Jamal Bousbaa, Talence (FR); Franck Choplin, Valennes (FR); Eliane Souteyrand, Ecully (FR); Jean-René Martin, Lozanne (FR); Jean-Pierre Cloarec, Lyons (FR)

(73) Assignee: Centre National da la Recherche Scientifique, Paris (FR)

( * ) Notice: Subject to any disclaimer, the term of this patent is extended or adjusted under 35 U.S.C. 154(b) by 0 days.

(21) Appl. No.: 10/181,636

(22) PCT Filed: Jan. 17, 2001

(86) PCT No.: PCT/FR01/00140

§ 371 (c)(1),
(2), (4) Date: Nov. 12, 2002

(87) PCT Pub. No.: WO01/53523

PCT Pub. Date: Jul. 26, 2001

(65) Prior Publication Data

US 2003/0138796 A1 Jul. 24, 2003

(30) Foreign Application Priority Data

Jan. 20, 2000 (FR) .......................................... 00 00697

(51) Int. Cl.$^7$ .......................... C12Q 1/68; C07H 21/00; C07H 21/02; C07H 21/04
(52) U.S. Cl. ........................... 435/6; 536/23.1; 536/25.3
(58) Field of Search ............................. 435/6; 536/23.1, 536/25.3

(56) References Cited

PUBLICATIONS

Maskos et al Nucleic Acids Research, 1992, vol. 20, No. 7 pp. 1679–1684.*
Lee et al. Langmuir, 1993, 9, pp. 3009–3014.*
International PCT Patent Application No. PCT/FR01/00139, filed Jan. 17, 2001, International Publication No. WO 01/00139, published Jul. 26, 2001.

(Continued)

Primary Examiner—Jezia Riley
(74) Attorney, Agent, or Firm—Welsh & Katz, Ltd.; Thomas W. Tolpin

(57) ABSTRACT

This invention concerns the use, for synthesizing and immobilising nucleic acids, of a solid support modified by an organized self-assembled monolayer of one or several organosilicon compounds. The invention also concerns methods for synthesizing and immobilizing nucleic acids on such a silanized solid support, and DNA chips obtained by said methods.

26 Claims, 8 Drawing Sheets

OTHER PUBLICATIONS

PCT International Search Report Jul. 5, 2001.

English translation of International PCT Patent Application No. PCT/FR01/00139, filed PCT/FR01/00139, filed Jan. 17, 2001, International Publication No. WO 01/00139, published Jul. 26, 2001.

Publication: *"Covalent Attachment Of Synthetic DNA To Self-Assembled Monolayer Films"*, by Linda A Chrisey, Gil U Lee and C. Elizabeth O'Ferral, of Naval Research Laboratory Washington, DC, published by Nucleic Acids Research, 1996, vol. 24, No. 15, pp. 3031–3039, XP-002149193.

Publication: *"Functionalized Siloxy-Anchored Monolayers With Exposed Amino, Azido, Bromo, or Cyano Groups"*, by Natarajan Balachanader and Chaim N. Sukenik of Chemistry Department, Case Western Reserve University, Cleveland, OH, presented at Tetrahedron Letters, vol. 29, No. 44, pp. 5593–5594, 1988, printed in Great Britain, XP-002149194.

Publication: *"Fabrication Of Patterned DNA Surfaces"*, by Linda A Chrisey, C. Elizabeth O'Ferral, Barry J. Spargo, Charles S. Dulcey and Jeffrey M. Calvert of Naval research Laboratory Washington, DC, published by Nucleic Acids Research, 1996, vol. 24, No. 15, pp. 3040–3047, XP002913337.

Publication: *"Synthesis Of Model Compounds For the Formation Of Self-Assembled Monolayers On A Silicon Surface"*, by Franz Effenberger and Stephan Heid of Institut for Organische Chemie Der Universitate, Stuttgart, Germany, Sep. 1995, pp. 1126–1130, XP-002149195.

\* cited by examiner

10

12

13

9

14

11

15

13

16

17   x = 20

18   x = 14

19   x = 25

20   x + y = 19

21   x + y = 24

22   x + y = 14

23

24

METHOD FOR SYNTHESIZING AND IMMOBILIZING NUCLEIC ACIDS ON A SILANIZED SOLID SUPPORT

CROSS REFERENCES TO RELATED APPLICATIONS

This application is based upon priority International Application PCT/FR01/00140 filed Jan. 17, 2001, International Publication No. WO 01/53523 A1 published Jul. 26, 2001, which is based upon priority French Application FR 00/00697 filed Jan. 20, 2000.

BACKGROUND OF THE INVENTION

The present invention relates to the use, for synthesizing or immobilizing nucleic acids, of a solid support modified with an organized self-assembled monolayer of one or more organosilicon compounds, and also to methods for synthesizing and immobilizing nucleic acids on a solid support.

To carry out chemical syntheses or immobilize molecules on an inorganic surface, it is, first of all, necessary to graft onto the surface coupling agents which will provide the attachment of the organic molecules to the inorganic substrates.

Organosilicon coupling agents have been proposed for this purpose by L. A. CHRISEY et al. (*Nucleic Acids Research*, 1996, 24, 15, 3031–3039) and U. MASKOS et al. (*Nucleic Acids Research*, 1992, 20, 7; 1679–1684). The agents used, namely 3-glycidoxypropyltrimethoxysilane and various aminosilanes, have, however, the drawback that they deposit randomly and nonreproducibly over the surface. They form a nonhomogeneous film thereon, the thickness of which, cannot be controlled, this film also not standing up very well to subsequent chemical treatments, the nonhomogeneity of the film in fact implying poor protection of the siloxane bonds. It is therefore very difficult to obtain reproducible grafting of these molecules. Before attaching or synthesizing oligonucleotides on the substrate, additional surface reactions are necessary to decrease the steric hindrance at the surface (for example grafting of bifunctional heterocyclic molecules, as described by L. A. CHRISEY et al.), to make the surface more hydrophilic (U. MASKOS et al. describe the grafting of ethylene glycol or penta- or hexaethylene glycol) and/or to overcome the poor reactivity of the surface functions, these being additional operations which, themselves, are also not controlled.

A. ULMAN described, in *Chem. Rev.,* 1996, 96, 1533–1554, the formation of organized self-assembled monolayers on solid supports using organosilicon compounds of the functionalized alkyltrichlorosilane type. The use thereof for attaching biomolecules is proposed, this being a method which probably requires, in this context, modification of the biomolecule with a thiol function and modification of the surface with heterobifunctional molecules.

BRIEF SUMMARY OF THE INVENTION

The inventors have given themselves the aim of overcoming the drawbacks of the prior art and of providing methods for synthesizing and immobilizing biomolecules, in particular nucleic acids, on solid supports modified with dense and organized monolayer films.

The subject of the present invention is the use, for synthesizing or immobilizing nucleic acids, of a solid support modified with an organized self-assembled monolayer comprising at least one organosilicon compound corresponding to formula (I):

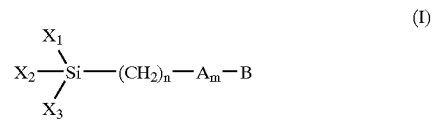

in which:

n is between 15 and 35, preferably between 20 and 25 m is equal to 0 or to 1, $X_1$, $X_2$ and $X_3$, which may be identical or different from one another, are selected from the group consisting of linear or branched, $C_1$ to $C_6$ saturated alkyl groups and hydrolyzable groups, at least one of $X_1$, $X_2$ or $X_3$ representing a hydrolyzable group, A represents the group —O—($CH_2$—$CH_2$—O)$_k$—($CH_2$)$_i$— in which k is between 0 and 100, preferably between 0 and 5, and i represents an integer greater than or equal to 0, preferably equal to 0 or to 1, when m=0, then B represents a group —OCOR, —OR or —COOR or a halogen atom, R representing a hydrogen atom or a linear or branched, $C_1$ to $C_6$ alkyl group, when m=1:

.if k=0 and i=0, then B represents a group $R_1$,

.if k=0 and i≧1, then B represents a group —$OR_1$, —$OCOR_1$, —$NR_1R_2$, —$COOR_1$, —$CONR_1R_2$ or —$SR_1$ or a halogen atom, .if k≧1 and i=0, then B represents a group —$R_1$, —$COR_1$, —COOR, or —$CONR_1R_2$, .if k≧1 and i≧1, then B represents a group —$OR_1$, —$OCOR_1$, —$NR_1R_2$, —$COOR_1$, —$CONR_1R_2$ or —$SR_1$ or a halogen atom, .$R_1$ and $R_2$, which may be identical or different, represent a hydrogen atom, a linear or branched, saturated or unsaturated, optionally substituted hydrocarbon-based chain comprising from 1 to 24 carbon atoms, or an aromatic group.

When B represents a group —$OR_1$, —$OCOR_1$, or —$COOR_1$, regardless of the values of i, and when k≧1, then it is clearly understood that B may represent any group resulting from the protection of a hydroxyl or carboxylic acid function, such as the protective groups described in *Protective groups in organic synthesis* (T. W. GREENE et al., 2nd edition, Wiley Interscience) for example a cyclic protective group.

For the purposes of the present invention and in the subsequent text, the term "nucleic acids" is intended to mean equally oligonucleotides and DNAs or RNAs, or even nucleic acids with a modified backbone of modified bases, such as peptide nucleic acids (PNAs) which involve peptide bonds instead of phosphodiester bonds.

The term "aromatic" is intended to mean any group which has one or more aryl rings, for example a phenyl ring. The expression "organized self-assembled monolayer" is intended to mean an assembly of molecules in which the molecules are organized, this organization being due to interactions and to strong cohesion between the chains of the molecules, giving rise to a stable and ordered anisotropic film (A. ULMAN, *Chem. Rev.,* 1996, 96, 1533–1554).

An organized self-assembled monolayer formed on a solid support makes it possible to produce a homogeneous, dense, organic surface with both chemically and structurally well-defined parameters. The formation of this monolayer, obtained due to the properties of self-assembly of the compounds of formula (I) for well-defined values of n, m, k and i, is completely reproducible for each organosilicon compound. In addition, the formation of a very dense, organized, self-assembled monolayer protects the siloxane bonds against chemical (acid or basic) treatments, which makes it possible to carry out varied chemical reactions on this surface.

The organosilicon compounds of formula (I) used in the present invention advantageously have very varied functionalities and great reactivity, in view of the nature of group A and of the diversity of the terminal groups B which can be used, it being possible, of course, for these groups B to be modified and functionalized as desired according to organic chemistry reactions well known to those skilled in the art.

The use according to the present invention makes it possible, particularly advantageously and by virtue of the organosilicon compounds of formula (I) selected, to synthesize or immobilize nucleic acids on a support reliably and reproducibly, in view of the homogeneity and of the stability of the organized self-assembled monolayer formed on the support. The nucleic acids are synthesized or immobilized on the modified support via strong covalent bonds, without degradation of the siloxane bonds developed between the organosilicon compounds and the solid support.

Suitable solid supports are, in general, those which have a hydrated surface and/or those which have a surface exhibiting hydroxyl groups. Preferably, said support is selected from the group consisting of glasses, ceramics (for example of the oxide type), metals (for example aluminum or gold) and metalloids (such as silicon).

For the purposes of the present invention, the term "hydrolyzable" is intended to mean any group capable of reacting with an acid in aqueous medium so as give the compounds $X_1H$, $X_2H$ or $X_3H$, $X_1$, $X_2$ and $X_3$ being as defined in formula (I).

According to an advantageous embodiment, said hydrolyzable group is selected from the group consisting of halogen atoms, the group —$N(CH_3)_2$ and the groups —OR', R' being a linear or branched, $C_1$ to $C_6$ saturated alkyl group.

With regard to the groups B and the hydrolyzable groups, suitable halogen atoms are equally fluorine and chlorine, bromine or iodine.

According to another advantageous embodiment, $X_1$, $X_2$ and $X_3$ represent chlorine atoms, n is equal to 22, m is equal to 1, i is equal to 0, k is equal to 1 or to 3 and B represents a group —$COCH_3$.

According to another advantageous embodiment, $X_1$, $X_2$ and $X_3$ represent chlorine atoms, n is equal to 22, m is equal to 1, i is equal to 1, k is equal to 2 and B represents a group —$COOCH_3$.

According to another advantageous embodiment, $X_1$, $X_2$ and $X_3$ represent chlorine atoms, n is equal to 16, 22 or 27, m is equal to 0 and B represents a group —$OCOCH_3$.

According to another advantageous embodiment, $X_1$, $X_2$ and $X_3$ represent chlorine atoms, n is equal to 21, m is equal to 0 and B represents a group —$COOCH_3$.

The use of modified solid supports according to the present invention is particularly advantageous for preparing DNA chips, i.e. supports to which a set of DNAs of known sequences is covalently attached in a very precise order, these chips being reusable many times. Such DNA chips make it possible, by hybridization of the DNAs immobilized on the support with target nucleic acids or oligonucleotides, to determine the sequence of these target molecules or to monitor gene expression. There are many applications: discovering novel genes and novel medicinal products, performing diagnoses, toxicity studies, etc.

A subject of the present invention is also a method for synthesizing nucteic acids on a solid support, characterized in that said support is modified with an organized self-assembled monolayer comprising at least one organosilicon compound corresponding to formula (I) as defined above, and in that it comprises the following steps:

a) preparing a solid support modified with an organized self-assembled monolayer comprising at least one organosilicon compound corresponding to formula (I) as defined above, in which said organosilicon compounds have, at their end, a protected amine or hydroxyl function;

b) optionally deprotecting the amine or hydroxyl function;

c) covalently coupling, in a localized manner, a nucleotide to the modified solid support obtained in step a) or b);

d) reiterating step c) at least once, with identical or different nucleotides.

Step a) is advantageously carried out via the following steps:

i) removing the contaminants from the solid support and hydrating and/or hydroxylating its surface, j) introducing an organosilicon compound of general formula (I) as defined above, into a mixture of at least two solvents comprising at least one nonpolar hydrocarbon-based solvent, under an inert atmosphere, said compound having, at one end, a protected amine or hydroxyl function, k) silanizing the support obtained in step i) by immersion in the solution prepared in step j), l) optionally annealing the silanized support obtained in step k), carrying the self-assembled monolayer, at a temperature between 50 and 120° C., for a period of 5 minutes to overnight, and m) rinsing the modified support obtained in step k) or l), with a solvent, preferably a polar solvent.

The term "contaminants" of the solid support is intended to mean any compound, such as fat, dust or others, which is present at the surface of the support and which is not part of the chemical structure of the support itself.

Depending on the nature of the solid support, step i) may be carried out using one or more solvents and/or oxidants and/or hydroxylating agents (for example a sulfochronic mixture), a detergent (for example Hellmanex), a photochemical treatment with ozone or any other suitable treatment.

In step j), by way of examples of protected amine or hydroxyl functions, mention may be made of the groups —NR'R" and —OCOR', in which R' and R" represent alkyl chains. Any other group resulting from the protection of an amine or hydroxyl function can also be envisaged.

Step j) may advantageously be carried out in a mixture of at least one nonpolar hydrocarbon-based solvent and at least one polar solvent. In this case, the volume proportions of nonpolar solvent and of polar solvent are preferably between 70/30 and 95/5.

By way of examples, and in a nonlimiting way, during step j), a nonpolar hydrocarbon-based solvent which can be used is cyclohexane and a polar solvent which can be used is chloroform.

In step j), the concentration of the organosilicon compound in the mixture of solvents is preferably between $1\times10^{-5}$ and $1\times10^{-2}$ mol/liter.

Step k) for the silanizing of the support may be carried out for a period of time of between 1 minute and 3 days and at a temperature of between −10° C. and 120° C. depending on the solvents used.

During the method for synthesizing nucleic acids on a solid support according to the present invention, step b) may be carried out by any technique known to those skilled in the art, for example by treatment with potassium hydroxide. Steps c) and d) may be carried out by phosphoramidite chemistry or by any other types of chemistry for covalently coupling nucleotides known to those skilled in the an, described, for example, by A. ELLINGTON and J. D. POLLARD in *Current Protocols in Molecular Biology*, John Wiley & Sons Inc., New York.

According to an advantageous embodiment of the method of synthesis according to the invention, a step for grafting, to the end of said organosilicon compounds, spacer arms carrying terminal amine or hydroxyl functions is carried out after step a) or b) and before step c).

Such spacer arms may be variable in charge, length and polarity, depending on the desired properties. For example, they may comprise a charged chain (such as a phosphoramidite with an abasic site), a noncharged hydrophilic chain (such as a polyethylene glycol), a noncharged hydrophobic chain (such as an alkyl chain) or a chain comprising an aqueous ammonia-labile group (such as the group —$SO_2$).

Step c) for covalently coupling a nucleotide to the modified support is carried out in a localized manner, i.e. at a given place on the support.

The reiteration of step c) may be carried out as many times as desired; step c) may, for example, be carried out about a hundred times, in the knowledge that the yield decreases beyond such a number.

The nucleotides coupled in steps c) and d) are preferably suitably protected, as described in the literature relating to oligonucleotide syntheses on solid supports. Subsequent to step d), it is clearly understood that the nucleic acids synthesized on the solid support may be deprotected by any suitable chemical treatment, for example aqueous ammonia. This treatment is not accompanied by cleavage of the nucleic acids from the support, unless an aqueous ammonia-labile spacer arm has been introduced between these nucleic acids and the silanized surface.

A subject of the present invention is also a method for immobilizing nucleic acids on a solid support, characterized in that said support is modified with an organized self-assembled monolayer comprising at least one organosilicon compound corresponding to formula (I) as defmed above, and in that it comprises the following steps:

a) preparing a solid support modified with an organized self-assembled monolayer comprising at least one organosilicon compound corresponding to formula (I) as defined above, in which said organosilicon compounds have, at their end, a protected amine or carboxylic acid function;

b) optionally deprotecting the amine or carboxylic acid function;

c) optionally, when the modified solid support carries terminal carboxylic acid functions, activating these functions;

d) bringing the modified solid support obtained in step a), b) or c) into contact with one or more solutions, applied locally, in one or more polar solvents, of the nucleic acid(s) to be immobilized, said nucleic acids carrying, at one of their ends, a spacer arm functionalized either with an amine function, when the modified solid support carries optionally protected terminal carboxylic acid functions, or with an activated carboxylic acid function, when the modified solid support carries optionally protected terminal amine functions; and e) washing the solid support on which said nucleic acids are immobilized.

Step a) is advantageously carried out as indicated above with respect to the method for synthesizing nucleic acids on a solid support, with the difference that, in step j), the organosilicon compound has, at one end, a protected amine or carboxylic acid function.

Step c) for activating the carboxylic acid functions may, for example, be carried out using a solution of N-hydroxysuccinimide or carbodiimide, or any other suitable activating reagent known to those skilled in the art.

During step d), it is clearly understood that, in order to solubilize the nucleic acids, any solution which allows good solubility of the latter and control of evaporation of the solution may be used; by way of example, and in a nonlimiting manner, mention may be made of an acetonitrile/water mixture. Each solution of nucleic acid to be immobilized is deposited at a given place on the support using a suitable means of microdeposition.

According to an advantageous embodiment of the immobilization method according to the invention, a step for grafting, to the end of said organosilicon compounds, spacer arms carrying terminal amine or carboxylic acid functions is carried out after step a) or b) and before step c). Suitable spacer arms are as described above.

A subject of the present invention is also a DNA chip, characterized in that it is obtained using the method for immobilizing nucleic acids according to the present invention, in which said nucleic acids are DNAs.

The DNA chip according to the invention has the advantage that it is stable and can therefore be reused in many hybridization and denaturation cycles.

Besides the arrangements above, the invention also comprises other arrangements which will emerge from the following description, which refers to examples of synthesis of organosilicon compounds which can be used in the context of the present invention and of synthesis or immobilization of nucleic acids on solid supports modified with an organized self-assembled monolayer of these organosilicon compounds, and also to the attached drawings.

DETAILED DESCRIPTION OF THE INVENTION

A detailed description of the preferred embodiments and best modes for practicing the invention are discussed herein along with some examples thereof.

It should be clearly understood, however, that these examples are given merely by way of illustration of the subject of the invention, of which they in no way constitute a limitation.

EXAMPLE 1

Synthesis of Organosilicon Compounds of Formula (I) in which m=1

Figure 1:
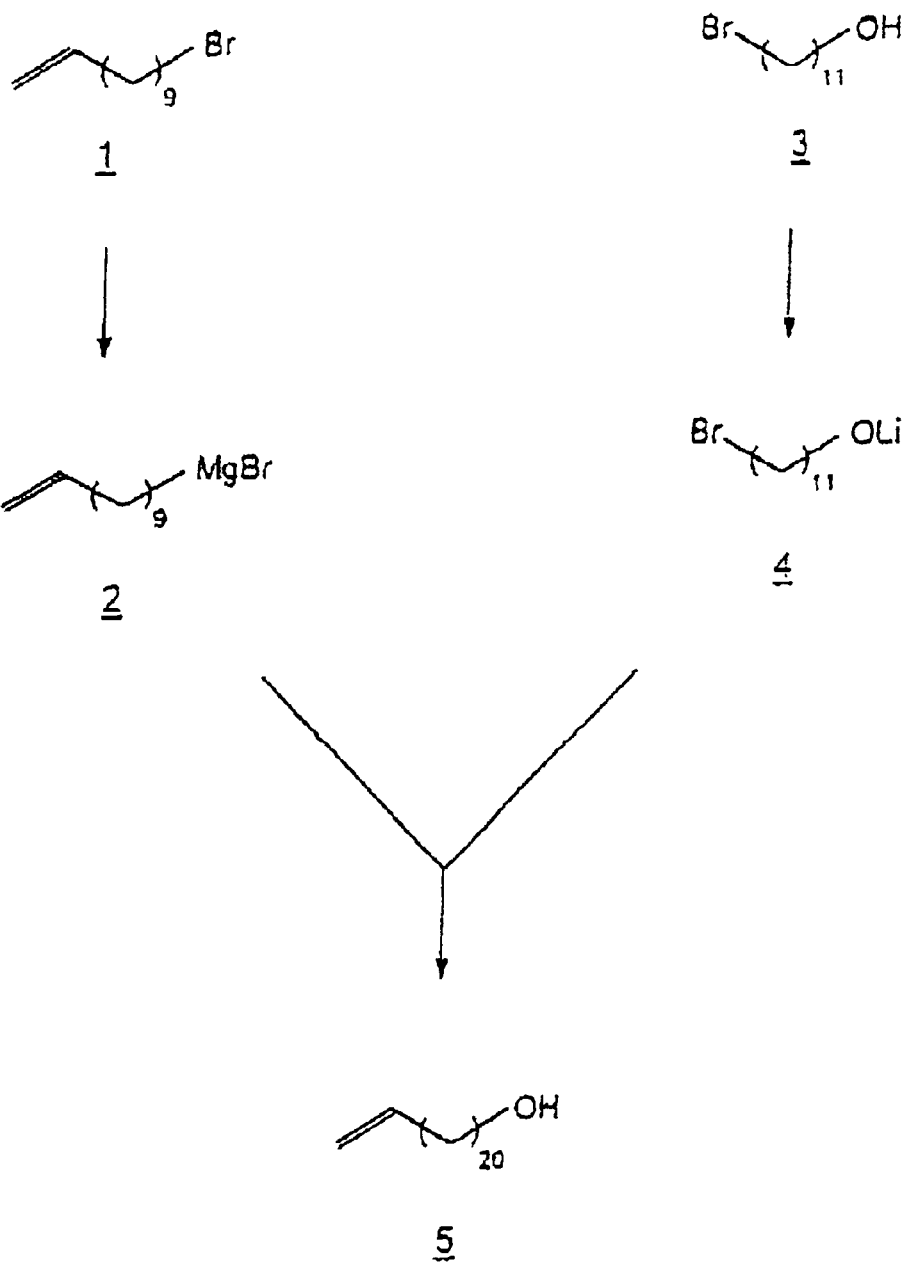
FIGS. 1, 2 and 3 illustrate the synthesis of unsaturated precursors of the organosilicon compounds of formula (I) in which m=1.

1) Synthesis of an Unsaturated Alcohol (FIG. 1)

Preparation of the Magnesium Compound 2

Magnesium (1.8 g; 70 mmol) is introduced into a 500-ml three-necked round-bottomed flask, under inert atmosphere. The unsaturated brominated derivative 1 (16.3 g; 70 mmol), dissolved beforehand in 70 ml of anhydrous THF (tetrahydrofuran), is added dropwise. A few drops of dibromoethane may be necessary to activate the magnesium. The reaction mixture is brought to reflux for 1 h 30 in order to obtain the magnesium compound 2, which will be used immediately.

Preparation of the Lithium Alkoxide 4

The bromoalcohol 3 (17.7 g; 70 mmol; 1 eq) is dissolved in 70 ml of anhydrous THF in a dry 250-ml three-necked round-bottomed flask under inert atmosphere. The solution is cooled to −78° C. and then methyllithium (50 ml; 80 mmol; 1.1 eq) is added dropwise. The lithium alkoxide 4 is obtained.

Preparation of the Unsaturated Alcohol 5

The magnesium compound 2 is cooled to −78° C. and then copper iodide (1.1 g; 3.5 mmol; 0.05 eq) is added. The solution is stirred for 25 minutes at −78° C. and then reheated to ambient temperature until a purple color is obtained. The solution is then immediately cooled to −78° C. and the lithium alkoxide 4 is introduced using a hollow needle under an argon atmosphere. The solution is stirred for 1 h at −78° C. and then for 18 h at ambient temperature. The excess methyllithium is destroyed by addition of ethanol, followed by hydrolysis in an acidic medium by addition of a 10% aqueous hydrochloric acid solution. The organic phase is extracted three times with diethyl ether. The ethereal phases are combined and washed with a 10% hydrochloric acid solution, with water and, finally, with a saturated aqueous $NaHCO_3$ solution. The organic phase is then washed to neutrality, dried over $MgSO_4$ and then concentrated under vacuum. The product is purified by reprecipitation from acetone. The compound 5 is obtained in the form of a white solid (19.8 g; melting point of 61.7–62.8° C.; yield of 87%). Its analysis by infrared and proton and carbon-13 NMR is as follows.

IR ($v(cm^{-1})$): 3330; 3079; 2919; 2851; 1642. $^1$H NMR ($CDCl_3$; δ (ppm)): 6.0–5.7 (m; 1H); 5.1–4.7 (m; 2H); 3.6 (t; 2H); 2.2–1.9 (m; 2H) and 1.7–1.2 (m; 37H, including 1H exchangeable with $D_2O$). $^{13}$C NMR ($CDCl_3$; δ (ppm)): 139.3; 113.8; 62.8; 33.6–25.8 (19 $CH_2$).

Figure 2:
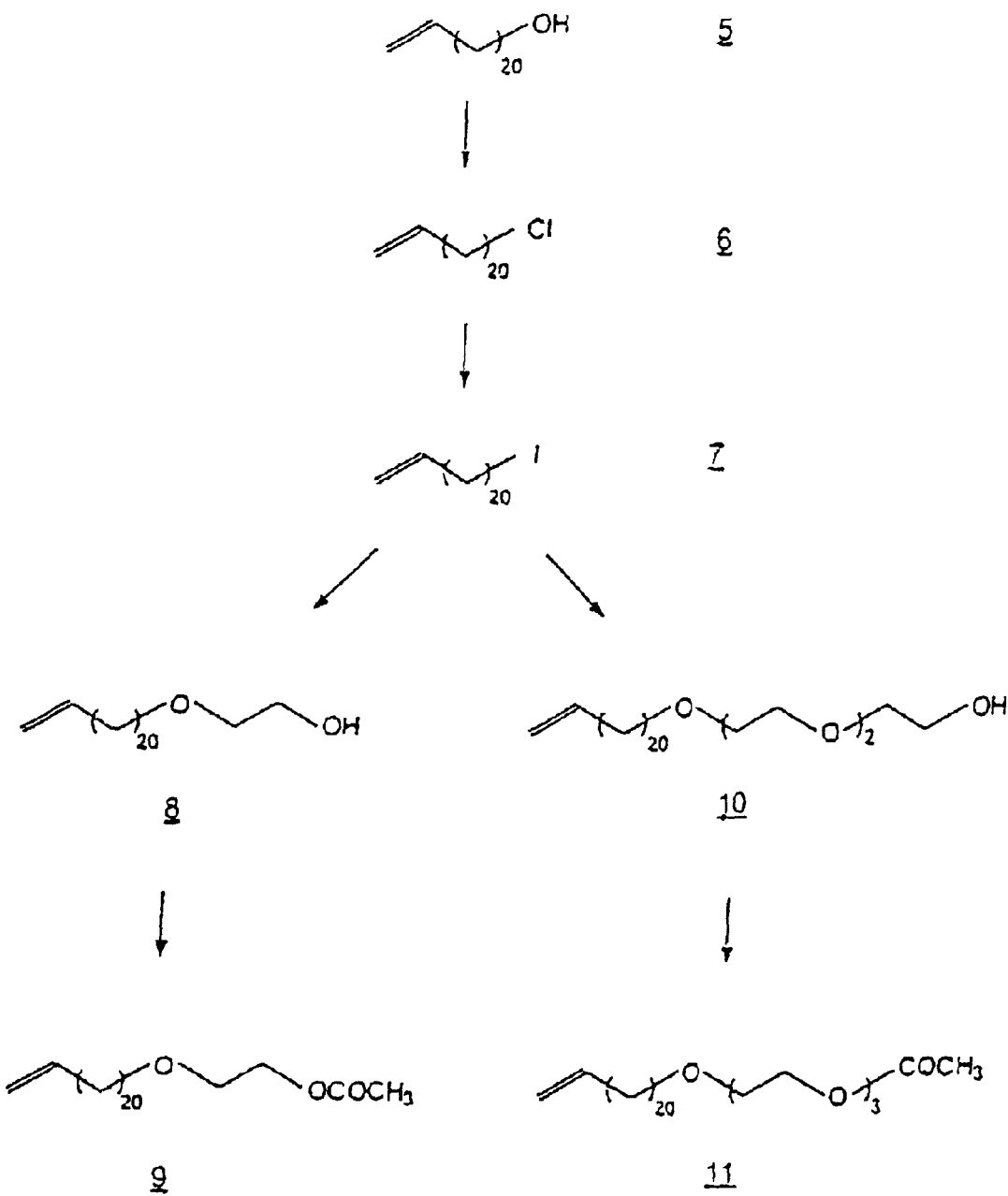

2) Introduction of an Ethylene Glycol ([f] FIG. 2)

Synthesis of the Unsaturated Chlorinated Derivative 6

The alcohol 5 obtained above (15 g; 46 mmol; 1 eq) and pyridine (40.36 ml; 6 mmol; 0.1 eq) are introduced into a 250-ml two-necked round-bottomed flask equipped with a magnetic stirrer and surmounted by a vertical reflux condenser. Thionyl chloride (6 ml; 70 mmol; 1.5 eq) is then added dropwise. The reaction medium is stirred for 1 h and is then brought to reflux until the OH band has completely disappeared (monitored by infrared spectroscopy). The reaction medium is subsequently hydrolyzed and then extracted three times with diethyl ether. The ethereal phases are combined and washed with a 10% hydrochloric acid solution, with water and then with a saturated $NaHCO_3$ solution. The ethereal phase is then washed to neutrality, dried over $MgSO_4$ and concentrated under vacuum. The compound 6 is obtained in the form of a yellow solid and is then purified by silica chromatography (eluent: petroleum ether/ether, 70/30 v/v); a white solid is obtained (14 g; melting point of 34.1–34.9° C.; yield of 75%). Its analysis by infrared and proton and carbon-13 NMR is as follows.

IR (dispersion in KBr) ν ($cm^{-1}$): 3076; 2917; 2849; 1641. $^1$H NMR ($CDCl_3$; δ (ppm)): 6.0–5.7 (m; 1H); 5.1–4.7 (m; 2H); 3.5–3.3 (t; 2H); 2.2–1.9 (m; 2H) and 1.7–1.2 (m; 36H). $^{13}$C NMR ($CDCl_3$; δ (ppm)): 139.2; 113.8; 33.8–25.6 (20 $CH_2$).

Synthesis of the Unsaturated Iodinated Derivative 7

The unsaturated chlorinated compound 6 (10.6 g; 32 mmol) and sodium iodide (22 g; 140 mmol; 4 eq) are solubilized in acetone (40 ml) in a 250-ml round-bottomed flask. The solution is then brought to reflux at 18 h. The reaction medium is then extracted with diethyl ether and the ethereal phases are combined, then washed with water, dried over $MgSO_4$ and concentrated under vacuum. The product is purified by operations of precipitation from acetone. The compound 7 is obtained in the form of a yellow solid (11 g; melting point of 41.1–42.0° C.; yield of 81%). Its analysis by infrared and proton and carbon-13 NMR is as follows.

IR (dispersion in KBr) ν ($cm^{-1}$): 3076; 2917; 2849; 1641. $^1$H NMR ($CDCl_3$; δ (ppm)): 6.0–5.7 (m; 1H); 5.1–4.7 (m; 2H); 3.2–3.0 (t; 2H); 2.2–1.9 (m; 2H) and 1.7–1.2 (m; 36H). $^{13}$C NMR ($CDCl_3$; δ (ppm)): 139.2; 113.8; 33.8–25.6 (20 $CH_2$).

Synthesis of the Unsaturated Alcohol 8

A solution of ethylene glycol (11.5 g; 180 mmol; 10 eq) and of sodium hydroxide (3.7 g; 90 mmol; 5 eq), reduced beforehand to a powder, in 20 ml of anhydrous THF is brought, to reflux for 30 minutes. The iodinated compound 7 (8 g; 18 mmol; 1 eq) and tetrabutylammonium hydrogen sulfate (0.62 g; 1.8 mmol; 0.1 eq) are added. The reaction medium is then brought to reflux for 72 h. After returning to ambient temperature, an aqueous hydrochloric acid solution (10%, 50 ml) is introduced. The reaction medium is then extracted three times with diethyl ether; the ethereal phases are combined and washed twice with a 10% hydrochloric acid solution, with water and then with a saturated $NaHCO_3$ solution. The ethereal phase is then washed to neutrality, dried over $MgSO_4$ and concentrated under vacuum. The solid obtained is reprecipitated in dichloromethane and then purified by silica chromatography (eluent: dichloromethane/ethyl acetate; v/v: 30/0). The compound 8 is obtained in the form of a white solid (1.4 g, melting point of 61.2–62.4° C.; yield of 21%). Its analysis by infrared and proton and carbon-13 NMR is as follows.

IR (dispersion in KBr) ν ($cm^{-1}$): 3330; 3080; 2917; 2849; 1643. $^1$H NMR ($CDCl_3$; δ (ppm)): 6.0–5.7 (m; 1H); 5.1–4.7 (m; 2H); 3.75–3.65 (m; 2H); 3.55–3.4 (m; 4H); 2.2–1.9 (m; 2H) and 1.7–1.0 (m; 37H, including 1H exchangeable with $D_2O$). $^{13}$C NMR ($CDCl_3$; δ (ppm)): 139.2; 113.8; 71.7 (2 $CH_2$); 63.7; 33.6–25.8 (19 $CH_2$).

Synthesis of the Unsaturated Alcohol Protected in the Ester Form 9

The unsaturated alcohol 8 (0.9 g; 2.7 mmol) is suspended in dichloromethane (10 ml) and triethylamine (0.6 ml; 5.4 mmol; 2 eq) in a 100-ml two-necked round-bottomed flask. The reaction medium is cooled to 0° C. and then acetyl chloride (0.5 ml; 4 mmol; 1.5 eq) is added dropwise using a syringe. The reaction medium is stirred for 15 minutes at 0° C. and then for 1 h 30 at ambient temperature. It is subsequently hydrolyzed and then extracted three times with diethyl ether. The ethereal phases arc combined and washed with a 10% hydrochloric acid solution, with water and then with a saturated NaHCO$_3$ solution. The ethereal phase is then washed to neutrality, dried over MgSO$_4$ and concentrated under vacuum. The compound 9 is obtained in the form of a white solid (0.9 g; yield of 100%). Its analysis by infrared and proton and carbon-13 NMR is as follows.

IR (dispersion in KBr) ν (cm$^{-1}$): 3080; 2917; 2849; 1742; 1643. $^1$H NMR (CDCl$_3$; δ (ppm)): 6.0–5.7 (m; 1H); 5.1–4.7 (m; 2H); 4.2–54.15 (m; 2H); 3.60–3.50 (t; 2H); 3.45–3.35 (t; 2H); 2.2–1.9 (m; 5H) and 1.7–1.0 (m; 36H). $^{13}$C NMR (CDCl$_3$; δ (ppm)): 172.0; 139.2; 113.8; 71.5; 68.5; 63.7; 33.6–25.8 (19 CH$_2$); 21.0.

3) Introduction of Three Ethylene Glycol Units (FIG. 2)

Starting from the unsaturated iodinated derivative 7 obtained above and from triethylene glycol, an unsaturated alcohol 10 is obtained and is then esterified to produce the product 11, this being carried out according to the same protocols as set out above.

The analysis of the product 10 by infrared and proton and carbon-13 NMR is as follows. IR (dispersion in KBr) ν (cm$^{-1}$): 3380; 3079; 2919; 2850; 1641. $^1$H NMR (CDCl$_3$; δ (ppm)): 5.9–5.7 (m; 1H); 5.1–4.7 (m; 2H); 4.3–4.2 (t; 2H); 3.7–3.4 (m; 10H); 3.4–3.3 (t; 2H); 2.2–1.9 (m; 5H) and 1.7–1.0 (m; 37H including 1H exchangeable with D$_2$O). $^{13}$C NMR (CDCl$_3$; δ (ppm)): 139.3; 114.0; 71.6–68.2 (6 CH$_2$); 63.6; 33.6–25.8 (19CH$_2$).

The analysis of the product 11 by infrared and proton and carbon-13 NMR is as follows. IR (dispersion in KBr) ν (cm$^{-1}$): 3079; 2919; 2850; 1740; 1641. $^1$H NMR (CDCl$_3$; δ (ppm)): 5.9–5.7 (m; 1H); 5.1–4.7 (m; 2H); 4.3–4.2 (t; 2H); 3.7–3.4 (m; 10H); 3.4–3.3 (t; 2H); 2.2–1.9 (m; 5H) and 1.7–1.0 (m; 36H). $^{13}$C NMR (CDCl$_3$; δ (ppm)): 171.5; 139.3; 114.0; 71.6–68.3 (6 CH$_2$); 63.6; 33.6–25.8 (19 CH$_2$); 21.0.

Figure 3:
Figure 3:
Figure 3:
Figure 3:
Figure 3:

4) Preparation of the Unsaturated Esters (FIG. 3)

Starting from the unsaturated alcohol 10 obtained above, the corresponding acid and the corresponding ester were prepared as follows.

Preparation of the Acid 12

The unsaturated alcohol 10 (3 g; 6.6 mmol) is suspended in 10 ml of acetone in a 100-ml three-necked round-bottomed flask. 80 ml of 2M Jones reagent (BOWDEN et al., *J. Chem. Soc.*, 1946, 39) are added to this suspension. The suspension is brought to reflux for 2 hours. After returning to ambient temperature, the acetone is evaporated and the solid is filtered off and then rinsed 5 times with water and 3 times with acetone cooled to 0° C. The solid is then purified by recrystallization from a THF/acetone mixture (v/v: 9/1) to give the compound 12 in the form of a white solid (2.9 g; yield of 94%). Its analysis by infrared and proton and carbon-13 NMR is as follows.

IR (dispersion in KBr) ν (cm$^{-1}$): 3370; 3080; 2917; 2849; 1707; 1643. $^1$H NMR (CDCl$_3$; δ (ppm)): 11.2 (s broad; 1H); 6.0–5.7 (m; 1H); 5.14.7 (m; 2H); 4.1–4.0 (s; 2H); 3.6–3.3 (m; 10H); 2.2–1.9 (m; 2H) and 1.7–1.0 (m; 36H). 13C NMR (CDCl$_3$; δ (ppm)): 172.1; 139.1; 114.0; 71.6–68.7 (5 CH$_2$); 63.5; 33.6–25.8 (19 CH$_2$).

Preparation of the Ester 13

The acid 12 (2.9 g; 6.4 mmol) is solubilized in anhydrous toluene (7 ml) under inert atmosphere at 0° C. in a 100-ml three-necked round-bottomed flask. Oxalyl chloride (1.22 g; 9.6 mmol; 1.5 eq) is introduced dropwise and then the mixture is stirred at ambient temperature for two hours. The excess reagent and the solvent are then evaporated under vacuum. The acyl chloride is temporarily stored under argon. Methanol (6 ml; 128 mmol; 20 eq), distilled before-hand over calcium chloride, is added slowly. The reaction medium is then brought to reflux for 18 h before being brought back to ambient temperature, and then the excess methanol is evaporated. The reaction medium is then extracted three times with diethyl ether. The ethereal phases are combined and washed with a 10% hydrochloric acid solution, with water and with a saturated NaHCO$_3$ solution. The ethereal phase is then washed to neutrality, dried over MgSO$_4$ and concentrated under vacuum. The compound 13 is obtained in the form of a white solid and is then purified by silica chromatography (eluent: petroleum ether/ether, 50/50 by volume). 300 mg of a white solid are obtained (yield of 10%). Its analysis by infrared and proton and carbon-13 NMR is as follows.

IR (dispersion in KBr) ν (cm$^{-1}$): 3080; 2917; 2849; 1742; 1643. $^1$H NMR (CDCl$_3$; δ (ppm)): 6.0–5.7 (m; 1H); 5.1–4.7 (m; 2H); 4.1–4.0 (s; 2H); 3.6–3.3 (m; 13H); 2.2–1.9 (m; 2H) and 1.7–1.0 (m; 36H). $^{13}$C NMR (CDCl$_3$; δ (ppm)): 171.8; 139.1; 114.0; 71.6–68.7 (5 CH$_2$); 63.6; 51.7; 33.6–25.8 (19 CH$_2$).

It is clearly understood that, by using the alcohol 8 comprising a single ethylene glycol unit, the corresponding acids and esters could also be obtained according to the same protocols as described here starting from the alcohol 10.

Figure 4:
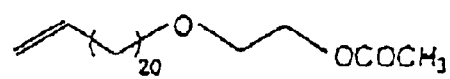
FIG. 4 illustrates the silylation of these unsaturated precursors.
Figure 4:
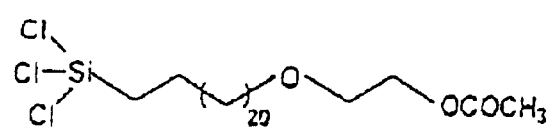
Figure 4:
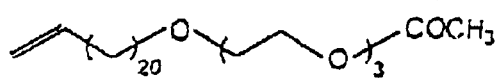
Figure 4:
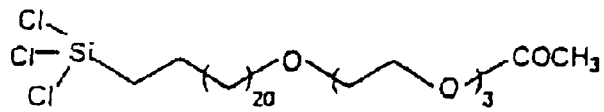
Figure 4:
Figure 4:
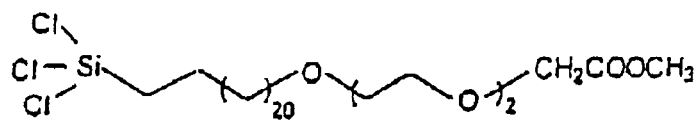

5) Silylation of the Unsaturated Precursors (FIG. 4)

The ester 9 (150 mg; 0.33 mmol) is introduced into a dry Schlenk tube under inert atmosphere. Freshly distilled trichlorosilane (0.3 ml; 2.2 mmol; 6 eq), anhydrous toluene (0.3 ml) and a drop of Karsted catalyst (PCO 72), sold by ABCR (reference 68478-92-2), are added. The reaction medium is then brought to 40° C. for 2 h. After returning to ambient temperature, the toluene and the excess trichlorosilane are evaporated under reduced pressure using a vane pump (pressure of 0.5 mmHg). The compound 14 is obtained in the form of a white solid and is stored under argon (yield of 99%). It is an organosilicon compound of formula (I) as defined above, in which X$_1$, X$_2$ and X$_3$ represent chlorine atoms, n is equal to 22, m is equal to 1, i is equal to 0, k is equal to 1 and B represents a group COCH$_3$. The analysis of the compound 14 by proton and carbon-13 NMR is as follows. $^1$H NMR (CDCl$_3$; δ (ppm)): 4.25–4.15 (m; 2H); 3.60–3.50 (t; 2H); 3.45–3.35 (t; 2H); 2.2–1.9 (s; 3H) and 1.7–1.0 (m; 42H). $^{13}$C NMR (CDCl$_3$; δ (ppm)): 171.0; 71.5; 68.5; 63.7; 31.9–22.3 (21 CH$_2$); 21.0.

By starting from the compound 11 obtained above and by using the same protocol, the corresponding organosilicon compound 15 is obtained. It is an organosilicon compound of formula (I) in which X$_1$, X$_2$ and X$_3$ represent chlorine atoms, n is equal to 22, m is equal to 1, i is equal to 0, k is equal to 3 and B represents a group —COCH$_3$. Its analysis by proton and carbon-13 NMR is as follows. $^1$H NMR (CDCl$_3$; δ (ppm)): 4.3–4.2 (t; 2H); 3.7–3.4 (m; 10H); 3.4–3.3 (t; 2H); 2.2–1.9 (s; 3H) and 1.7–0.9 (m; 42H). $^{13}$C NMR (CDCl$_3$; δ (ppm)): 171.2; 71.6–68.1 (6 CH$_2$); 63.6; 31.9–22.3 (21 CH$_2$); 21.0.

By starting from the compound 13 obtained above and by using the same protocol, the corresponding organosilicon compound 16 is obtained. It is a compound of formula (I) in which X$_1$, X$_2$ and X$_3$ represent chlorine atoms, n is equal to 22, m is equal to 1, i is equal to 1, k is equal to 2 and B represents a group —COOC$_3$. Its analysis by proton and carbon-13 NMR is as follows. $^1$H NMR (CDCl$_3$; δ (ppm)): 4.1–4.0 (s; 2H); 3.6–3.3 (m; 13H); 1.7–0.9 (m; 42H). $^{13}$C NMR (CDCl$_3$; δ (ppm)): 171.0; 71.6–63.8 (6 CH$_2$); 51.7; 31.9–22.3 (21 CH$_2$).

Table I below recapitulates the structure of the organosilicon compounds of formula (I) obtained in the present example.

TABLE I

| Organosilicon compound | $X_1, X_2, X_3$ | n | m | k | i | B |
|---|---|---|---|---|---|---|
| 14 | Cl | 22 | 1 | 1 | 0 | —COCH$_3$ |
| 15 | Cl | 22 | 1 | 3 | 0 | —COCH$_3$ |
| 16 | Cl | 22 | 1 | 2 | 1 | —COOCH$_3$ |

EXAMPLE 2

Synthesis of Organosilicon Compounds of Formula (I) in which m=0

Figure 5:
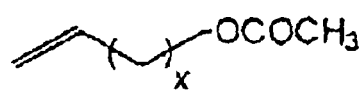
FIG. 5 represents unsaturated precursors of organosilicon compounds of formula (I) in which m=0.
Figure 5:
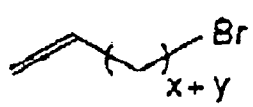
Figure 5:
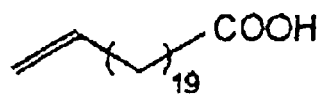
Figure 5:
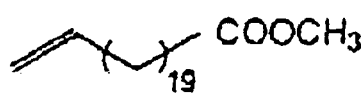

1) Synthesis of Unsaturated Precursors ([f] FIG. 5)

1-1: Unsaturated Precursors Carrying a Group —OCOCH$_3$

Compound 17

The unsaturated alcohol 5 obtained in example 1 (0.9 g; 2.7 mmol) is suspended in dichloromethane (10 ml) and triethylamine (0.6 ml; 5.4 mmol; 2 eq) in a 100-ml two-necked round-bottomed flask. The reaction medium is cooled to 0° C. and then acetyl chloride (0.5 ml; 4 mmol; 1.5 eq) is added dropwise using a syringe. The reaction medium is stirred for 15 minutes at 0° C. and then for 1 h 30 at ambient temperature. The reaction medium is subsequently hydrolyzed and then extracted three times with diethyl ether. The ethereal phases are combined, and washed with a 10% hydrochloric acid solution, with water and then with a saturated NaHCO$_3$ solution. The ethereal phase is then washed to neutrality, dried over MgSO$_4$ and concentrated under vacuum. The compound 17 is obtained in the form of a white solid (0.9 g; yield of 100%). Its analysis by infrared and proton and carbon-13 NMR is as follows.

IR (dispersion in KBr) ν (cm$^{-1}$): 3079; 2919; 2850; 1740; 1641. $^1$H NMR (CDCl$_3$; δ (ppm)): 5.9–5.7 (m; 1H); 5.1–4.7 (m; 2H); 4.1–3.9 (t; 2H); 2.2–1.9 (m; 5H) and 1.7–1.0 (m; 36H). $^{13}$C NMR (CDCl$_3$; δ (ppm)): 171.1; 139.3; 114.0; 64.7; 33.6–25.8 (19 CH2); 21.0.

Compound 18

By using the same protocol as for the production of the compound 17, but starting from an unsaturated alcohol comprising 16 carbon atoms, the compound 18 is obtained, the analysis of which by infrared and proton and carbon-13 NMR is as follows: IR (dispersion in KBr) ν (cm$^{-1}$): 3080; 2923; 2853; 1742; 1643. $^1$H NMR (CDCl$_3$; δ (ppm)): 5.9–5.7 (m; 1H); 5.1–4.7 (m; 2H); 4.1–4.0 (t; 2H); 2.1–1.9 (m; 5H) and 1.7–1.1 (m; 24H). $^{13}$C NMR (CDCl$_3$; δ (ppm)): 171.1; 139.3; 114.0; 64.8; 33.6–25.8 (13 CH$_2$); 21.2.

Compound 19

By using the same protocol for the production of the compound 17, but starting from an unsaturated alcohol comprising 27 carbon atoms, the compound 19 is obtained, the analysis of which by infrared and proton and carbon-13 NMR is as follows: IR (dispersion in KBr) ν (cm$^{-1}$): 3080; 2923; 2853; 1742; 1643. $^1$H NMR (CDCl$_3$; δ (ppm)): 5.9–5.7 (m; 1H); 5.14.7 (m; 2H); 4.1–4.0 (t; 2H); 2.1–1.9 (m; 5H) and 1.7–1.1 (m; 46H). $^{13}$C NMR (CDCl$_3$; δ (ppm)): 171.1; 139.3; 114.0; 64.8; 33.625.8 (24 CH$_2$); 21.1.

1-2: Brominated Unsaturated Precursors

Starting from unsaturated brominated derivatives of formula CH$_2$=CH—(CH$_2$)$_x$Br, x being between 3 and 23, and following the protocol for the production of the compound 2 as described in example 1, organomagnesium compounds of formula CH$_2$=CH—(CH$_2$)$_x$MgBr are obtained. The coupling thereof with a dibrominated derivative Br(CH$_2$)$_y$Br (x+y being equal to a minimum of 13 and to a maximum of 33) under the same conditions as those for the coupling with a bromoalcohol in accordance with example 1 for the production of the compound 5, produces the unsaturated brominated derivatives of formulae 20, 21 and 22.

The compound 20 is obtained using an unsaturated brominated derivative in which x is equal to 9 and a dibrominated derivative in which y is equal to 10. Its analysis by infrared and proton and carbon-13 NMR is as follows: IR (dispersion in KBr) ν (cm$^{-1}$): 3078; 2922; 2852; 1640. $^1$H NMR (CDCl$_3$; δ (ppm)): 5.9–5.7 (m; 1H); 5.1–4.9 (m; 2H); 3.5 (t; 2H); 2.2–1.8 (m; 4H) and 1.6–1.2 (m; 32H). $^{13}$C NMR (CDCl$_3$; δ (ppm)): 139.2; 114.1; 33.9–25.7 (19 CH$_2$).

The compound 21 is obtained using an unsaturated brominated derivative in which x is equal to 14 and a dibrominated derivative in which y is equal to 10. Its analysis by infrared and proton and carbon-13 NMR is as follows: IR (dispersion in KBr) ν (cm$^{-1}$): 3080; 2920; 2851; 1642. $^1$H NMR (CDCl$_3$; δ (ppm)): 6.0–5.7 (m; 1H); 5.1–4.9 (m; 2H); 3.5 (t; 2H); 2.2–1.8 (m; 4H) and 1.6–1.2 (m; 42H). $^{13}$C NMR (CDCl$_3$; δ (ppm)): 138.8; 113.8; 33.9–25.7 (24 CH$_2$).

The compound 22 is obtained using an unsaturated brominated derivative in which x is equal to 9 and a dibrominated derivative in which y is equal to 5. Its analysis by infrared and proton and carbon-13 NMR is as follows: IR (dispersion in KBr) ν (cm$^{-1}$): 3078; 2925; 2854; 1641. $^1$H NMR (CDCl$_3$; δ (ppm)): 5.9–5.7 (m; 1H); 5.1–4.9 (m; 2H); 3.5 (t; 2H); 2.2–1.8 (m; 4H) and 1.6–1.2 (m; 22H). $^{13}$C NMR (CDCl$_3$; δ (ppm)): 139.2; 114.1; 33.9–25.7 (14 CH$_2$).

1-3: Unsaturated Precursors Carrying a Carboxylic Acid Group —COOH

The unsaturated alcohol 5 obtained in example 1 (13 g; 40 mmol) is suspended in 40 ml of acetone in a 250-ml three-necked round-bottomed flask. 80 ml of Jones reagent (2M) are added to this suspension. The suspension is brought to reflux for 2 hours. After returning to ambient temperature, the acetone is evaporated and the solid is filtered and then rinsed 5 times with water and 3 times with acetone cooled to 0° C. The solid is then purified by recrystallization from a THF/acetone mixture (v/v: 9/1) to give the compound 23 in the form of a white solid (9.9 g; melting point of 73–74° C.; yield of 94%). Its analysis by infrared and proton and carbon-13 NMR is as follows: IR (dispersion in KBr) ν (cm$^{-1}$): 3370; 3080; 2917; 2849; 1707; 1643. $^1$H NMR (CDCl$_3$; δ (ppm)): 11.2 (s broadened; 1H); 6.0–5.7 (m; 1H); 5.1–4.9 (m; 2H); 2.4 (t; 2H); 2.2–2.0 (m; 2H) and 1.9–1.1 (m; 34H). $^{13}$C NMR (CDCl$_3$; δ (ppm)): 172.0; 139.3; 113.8; 33.6–25.8 (19 CH$_2$).

1-4: Unsaturated Precursors Carrying a Methyl Ester Group COOCH$_3$

The acid 23 obtained above (4 g; 11.8 mmol) is solubilized in anhydrous toluene (20 ml) under an inert atmosphere at 0° C. in a 100-ml three-necked round-bottomed flask. Oxalyl chloride (2 g; 17.6 mmol; 1.5 eq) is introduced dropwise and the mixture is then stirred at ambient temperature for two hours. The excess reagent and the solvent are then evaporated under vacuum. The acyl chloride is temporarily stored under argon. Methanol (10 ml; 236 mmol; 20 eq), distilled beforehand over calcium chloride, is added slowly. The reaction medium is then brought to reflux for 18 hours. After the reaction mixture has returned to ambient temperature the excess methanol is evaporated. The reaction medium is then extracted three times with diethyl ether. The ethereal phases are combined, and washed with a 10% hydrochloric acid solution, with water and with a saturated $NaHCO_3$ solution. The ethereal phase is then washed to neutrality, dried over $MgSO_4$ and concentrated under vacuum. The compound 24 is obtained in the form of a white solid (4 g; melting point of 50–51.5° C.; yield of 100%). Its analysis by infrared and proton and carbon-13 NMR is as follows: IR (dispersion in KBr) ν ($cm^{-1}$): 3080; 2917; 2849; 1743; 1643. $^1H$ NMR ($CDCl_3$; δ (ppm)): 6.0–5.7 (m; 1H); 5.1–4.9 (m; 2H); 3.6 (t; 3H); 2.4–2.3 (t; 2H); 2.2–2.0 (m; 2H) and 1.9–1.1 (m; 34H). $^{13}C$ NMR ($CDCl_3$; δ (ppm)): 172.3; 139.3; 114.0; 51.5; 33.6–25.8 (19 $CH_2$).

2) Silylation of the Unsaturated Precursors

The same protocol as that indicated in example 1 is carried out. The proton and carbon-13 NMR spectra of the organosilicon compounds obtained starting from the unsaturated precursors 17, 18 and 19 are as follows:

starting from the precursor 17: $^1H$ NMR ($CDCl_3$; δ (ppm)): 4.1–3.9 (t; 2H); 2.1 (s; 3H); 1.7–0.9 (m; 42H). $^{13}C$ NMR ($CDCl_3$; δ (ppm)): 171.2; 64.7; 31.9–22.3 (21 $CH_2$); 21.0.

starting from the precursor 18: $^1H$ NMR ($CDCl_3$; δ (ppm)): 4.1–3.9 (t; 2H); 2.1 (s; 3H); 1.7–0.9 (m; 30H). $^{13}C$ NMR ($CDCl_3$; δ (ppm)): 171.2; 64.7; 31.9–22.3 (15 $CH_2$); 21.0.

starting from the precursor 19: $^1H$ NMR ($CDCl_3$; δ (ppm)): 4.1–3.9 (t; 2H); 2.1 (s; 3H); 1.7–0.9 (m; 52H). $^{13}C$ NMR ($CDCl_3$; δ (ppm)): 171.2; 64.7; 31.9–22.3 (26 $CH_2$); 21.0.

Table II below recapitulates the structure of the organosilicon compounds of formula (I) obtained in the present example.

TABLE II

| Silylation of precursor No. | $X_1$, $X_2$, $X_3$ | n | m | B |
|---|---|---|---|---|
| 17 | Cl | 22 | 0 | —$OCOCH_3$ |
| 18 | Cl | 16 | 0 | —$OCOCH_3$ |
| 19 | Cl | 27 | 0 | —$OCOCH_3$ |
| 24 | Cl | 21 | 0 | —$COOCH_3$ |

EXAMPLE 3

Silanization of a Solid Support Using an Organosilicon Compound of Formula (I) and Production of an Organized Self-assembled Monolayer 1) Silanization of the Solid Support A surface-oxidized silicon disc is used as substrate. The disc is cleaned according to the following procedure, in order to remove the contaminants from its surface and to hydrate it:

immersion in a freshly prepared chromium(VI)/sulfuric acid mixture (2.5 g of $K_2Cr_2O_4$; 2.5 ml of distilled water; 50 ml of sulfuric acid) for 10 minutes, under a laminar flow hood equipped with dust filters, the disc is immersed in dionized water and subjected to ultrasound for 20 minutes. This process is repeated twice with durations of sonication of 5 and 2 minutes, respectively, under a laminar flow hood equipped with dust filters, the disc is introduced into the silanization reactor in order to be dried, under an inert and filtered atmosphere. The reactor is immersed for 45 minutes in an oil bath at 100° C. and then is removed from the oil bath and its temperature is brought back to 18° C.

The organosilicon compound 14 obtained in example 1, freshly prepared in the desired amount, under an inert atmosphere, is dissolved in a fraction of a $C_6H_{12}/CCl_4/CHCl_3$ (v/v/v: 80/12/8) mixture. The organosilicon compound 14 in solution is subsequently withdrawn with a syringe and then introduced into a Schlenck tube containing the remainder of the solvent mixture, the total volume of which has been calculated so as to produce a silanization solution of appropriate dilution (between $1\times10^{-5}$ and $1\times10^{-2}$ mol/liter). The solvents were dried beforehand according to procedures known per se.

The silanization solution is introduced, with a syringe, into the reactor and the silicon disc remains immersed in this solution for 16 h. The silanized disc is withdrawn from the reactor, and is then optionally annealed, after having been washed with chloroform (HPLC grade), at a temperature of between 50 and 120° C. It is then cleaned with ultrasound for 2 minutes, this process being repeated twice.

2) Characterization of the Modified Surface

A solid support, the surface of which is modified with the compound 14, was obtained above. The grafting of the organosilicon compounds is monitored using confocal Raman spectroscopy and infrared spectroscopy.

3) Release of the Surface Hydroxyls

If necessary, the surface hydroxyls can be released using the following protocol: the silanized disc is immersed in a solution of KOH (0.5 M) in a water/ethanol (v/v: 1/1) mixture for 20 minutes. The disc is then cleaned with ultrasound for 5 minutes in demineralized water. This process is repeated once in water and then a second time in chloroform.

4) Characterization of the Surface After Release of the Hydroxyls

Figure 6:
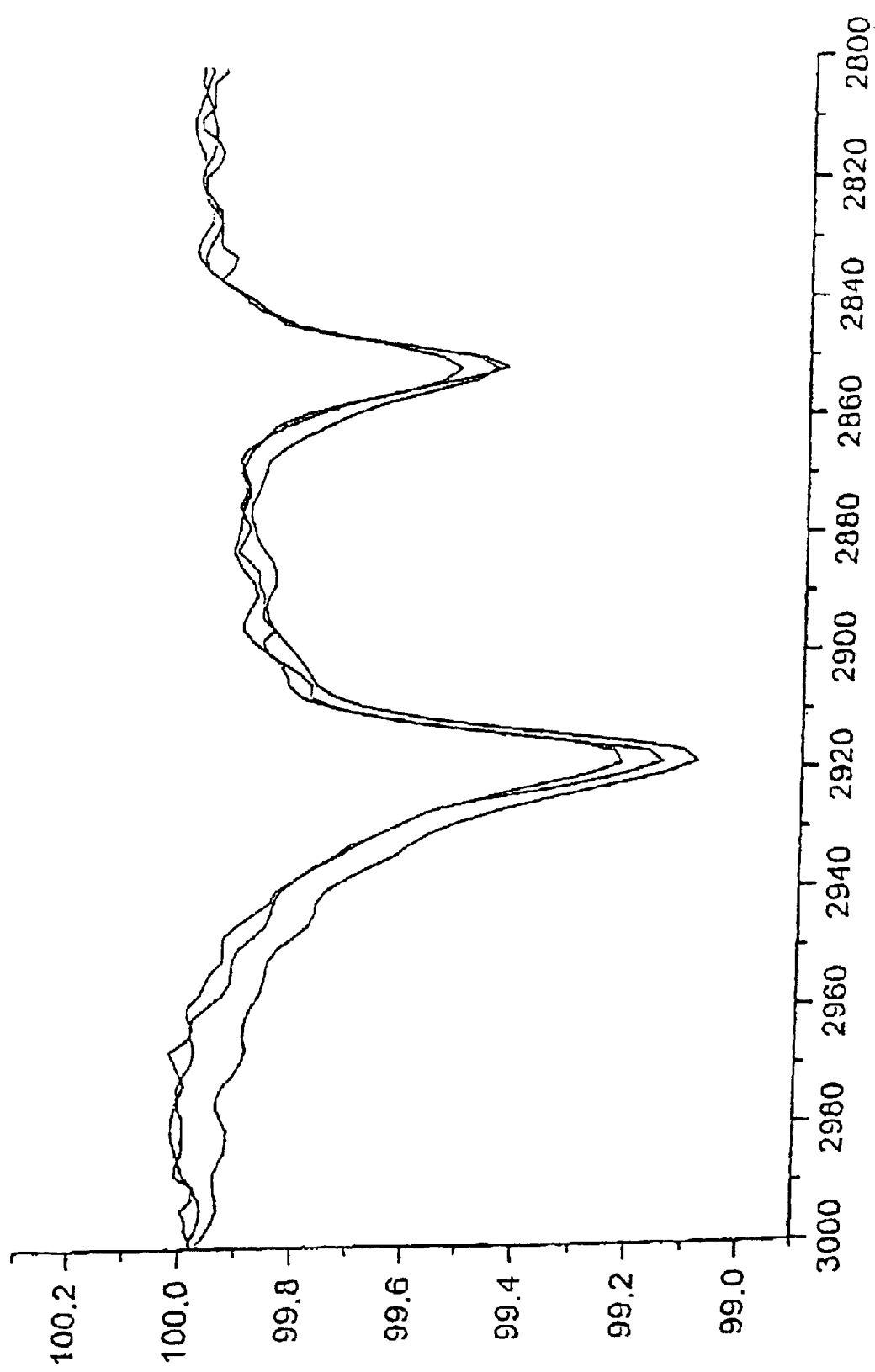
FIG. 6 represents infrared spectra produced after three experiments consisting of grafting the organosilicon compound 14 onto the silica surface of Au/Si/$SiO_2$ substrates.

FIG. 6 represents infrared spectra obtained after three experiments of grafting the compound 14 onto the support, according to the silanization protocol set out above and after saponification-of the surface esters. The transmission appears on the y-axis and the frequency ($cm^{-1}$) appears on the x-axis. It is noted that the three spectra are superimposed, with peaks characteristic of an organized system at 2917 and at 2850 $cm^{-1}$. Thus, it may be concluded therefrom that the grafting of the organosilicon compound onto the support is reproducible and gives rise to the formation of an organized self-assembled monolayer.

Figure 7B:
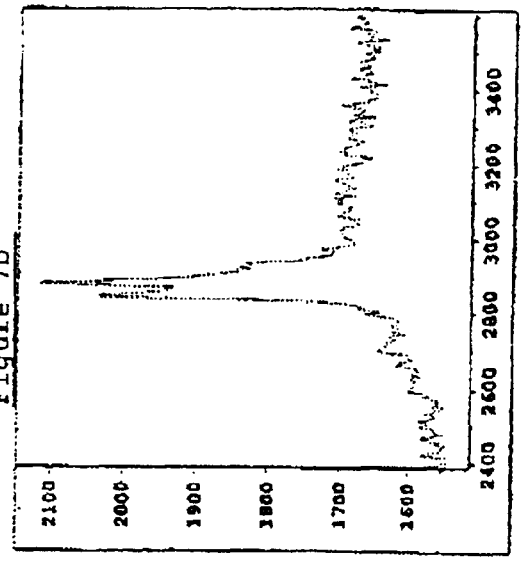
FIGS. 7b and 7c represent the Raman spectra taken at two different points of this surface.
Figure 7C:
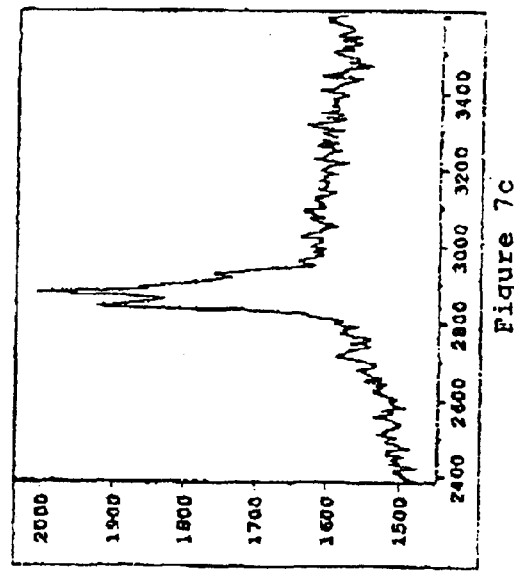
Figure 7A:
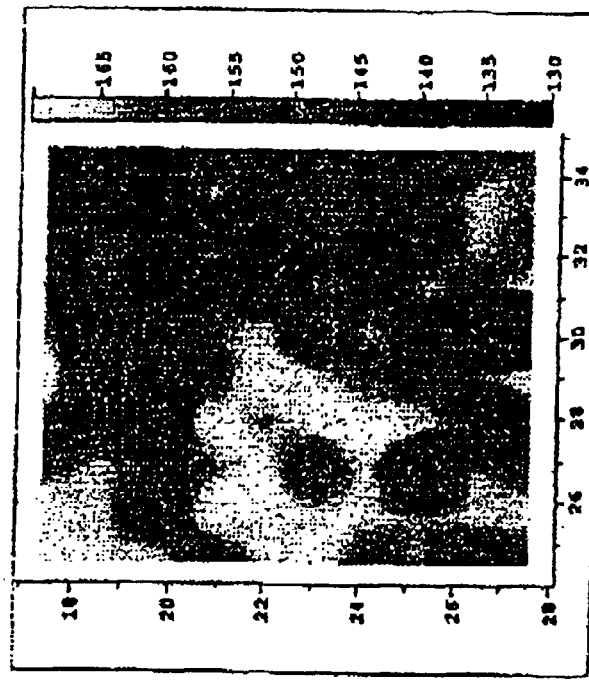
FIG. 7a represents the density, analyzed by Raman spectroscopy, of the surface of the Au/Si/$SiO_2$ substrate onto which the organosilicon compounds 14 are grafted.

FIG. 7 represents Raman spectroscopic studies of the modified surface obtained above. FIG. 7a is representative of the density of the surface of the grafted substrate, the dimensions of the surface appearing on the x-axis and on the y-axis (7 mm in the figure correspond to 1 μm on the substrate) and the scale of the density being graduated from 130 to 165 (arbitrary units). This figure demonstrates the homogeneity of the surface. FIGS. 7b and 7c represent the Raman spectra taken at two different points of the surface of the substrate; the y-axes represent counts per second and the frequency appears on the x-axes.

The infrared and Raman spectra therefore unambiguously show the homogeneity of the film deposited on the substrate and also the organization of the molecules on the surface, characteristic of an organized self-assembled monolayer. The infrared spectrum also shows that the grafting of the film is completely reproducible.

EXAMPLE 4

Another Example of Silanization of a Solid Support Using an Organosilicon Compound of Formula (I)

A glass microscope slide is used as substrate. The glass slide is cleaned by immersion in a 2% aqueous Hellmanex solution (marketed by Polylabo under the reference 12240) for 2 h at 20° C., followed by thorough rinsing with deionized water. Under a laminar flow hood equipped with dust filters, the glass slide is introduced into the grafting reactor in order to be dried, under an inert and filtered atmosphere. The reactor is immersed for 45 minutes in an oil bath at 100° C., and is then removed from the oil bath and its temperature is brought back to 18° C.

The silanization solution, prepared using the organosilicon compound 14 as indicated in the previous example, is introduced, with a syringe, into the reactor and the glass slide remains immersed in this solution for 16 h. The silanized substrate is rinsed as described in example 3.

The characterization of the surface by infrared and Raman spectroscopy here again demonstrates the production of an organized self-assembled monolayer on the substrate, the same results also being obtained with organosilicon agents of formula (I) other than the compound 14.

EXAMPLE 5

Direct Synthesis of Nucleic Acids on a Solid Support Modified with an Organized Self-assembled Monolayer of Organosilicon Compounds of Formula (I)

1) Preparation of the Solid Support Modified with an Organized Self-assembled Monolayer The solid support used is an oxidized silicon substrate Si/SiO$_2$ on which an organized self-assembled monolayer comprising the organosilicon compound 14 has been formed, according to the protocol indicated in example 3. Any other organosilicon compound of formula (I) may also be used, as may any mixture of organosilicon compounds comprising at least one organosilicon compound of formula (I).

The ends of the organosilicon compounds grafted onto the support are converted to hydroxyl groups by immersion of the substrate in a solution of KOH, as indicated in example 3. A substrate comprising surface hydroxyl functions is thus obtained. The substrate is cleaned in acetonitrile and is subjected to ultrasound for I minute before being placed in the synthesis chamber.

2) Synthesis of Nucleic Acids on this Support

Phosphoramidite chemistry is used here, in the knowledge that other types of chemistry well known to those skilled in the art may be used, such as H-phosphonate chemistry. The nucleotides are therefore used in the form of β-cyanoethylphosphoramidites, the amines of the various nitrogen-containing bases being protected, for example and in a nonlimiting manner, with benzoyl, isobutyryl or tert-butylphenoxyacetic groups. The nucleotides are protected in the 5' position with a dimethoxytrityl group; use may, however, also be made of photolabile groups (such as MeNPOC described by Pease et al. in *Proc. Natl. Acad. Sci. USA*, 1994, 91, 5022–5026), which may be removed by UV illumination.

The nucleic acid synthesis is, with the phosphoramidite chemistry used, carried out in the 3'→5' direction. The various steps for grafting a nucleotide are as follows, all of these steps constituting a cycle:

7. detritylation (25 seconds): 3% trichloroacetic acid in dichloromethane;

8. washing: anhydrous acetonitrile;

9. coupling (1 minute): introduction of a mixture of 0.1 M amidite and of an activator at 0.45 M (tetrazole);

10. capping (15 seconds): introduction of a mixture of (i) acetic anhydride/2,6-lutidine/acetonitrile (10 ml/10 ml/80 ml) and (ii) 1-methylimidazole at 10% in dimethylformamide (10 ml/90 ml), 11. oxidation (15 seconds): introduction of an iodine/pyridine/tetrahydrofuran/water (0.508 mg/1.6 ml/15.2 ml/3.2 ml) mixture;

12. capping (15 seconds).

It is clearly understood that, in the cycle given above, the detritylation, washing, coupling, capping and oxidation solutions are not given in a limiting manner.

As many cycles as desired may be carried out, depending on the length of the nucleic acid intended to be produced. Once the final number of cycles has been reached, the nitrogen-containing bases are deprotected and the nucleic acid is deprotected by treatment with 30–33% aqueous ammonia overnight at ambient temperature, so as to cleave the protective groups distributed on the backbone and the nitrogen-containing bases. Optionally, if an aqueous ammonia-labile spacer arm has been introduced between a part of the nucleic acids and the silanized surface, this fraction of the nucleic acids will be cleaved from the support.

Depending on the nature of the protective groups used, it may be possible to use other deprotection treatments, for example using potassium carbonate.

The substrate is washed with water and then with TRIS buffer (solution of 10 mM TRIS HCl adjusted to pH 7.1 by adding a 10 mM TRIS base solution, the final solution having an NaCl concentration of 50 mM) before it can be used for a hybridization.

EXAMPLE 6

Hybridization Experiments Carried out with Oligonucleotides Synthesized Directly on a Solid Support Following the Method According to the Present Invention A solid support modified with an organized self-assembled monolayer as described in example 5 (oxidized silicon Si/SiO$_2$ on which a monolayer of organosilicon compounds 14 is formed, the surface functions having been converted to hydroxyl groups) is used. A spacer arm of 10 nucleotides T is grafted onto this modified support before the oligonucleotide synthesis.

Figure 8:
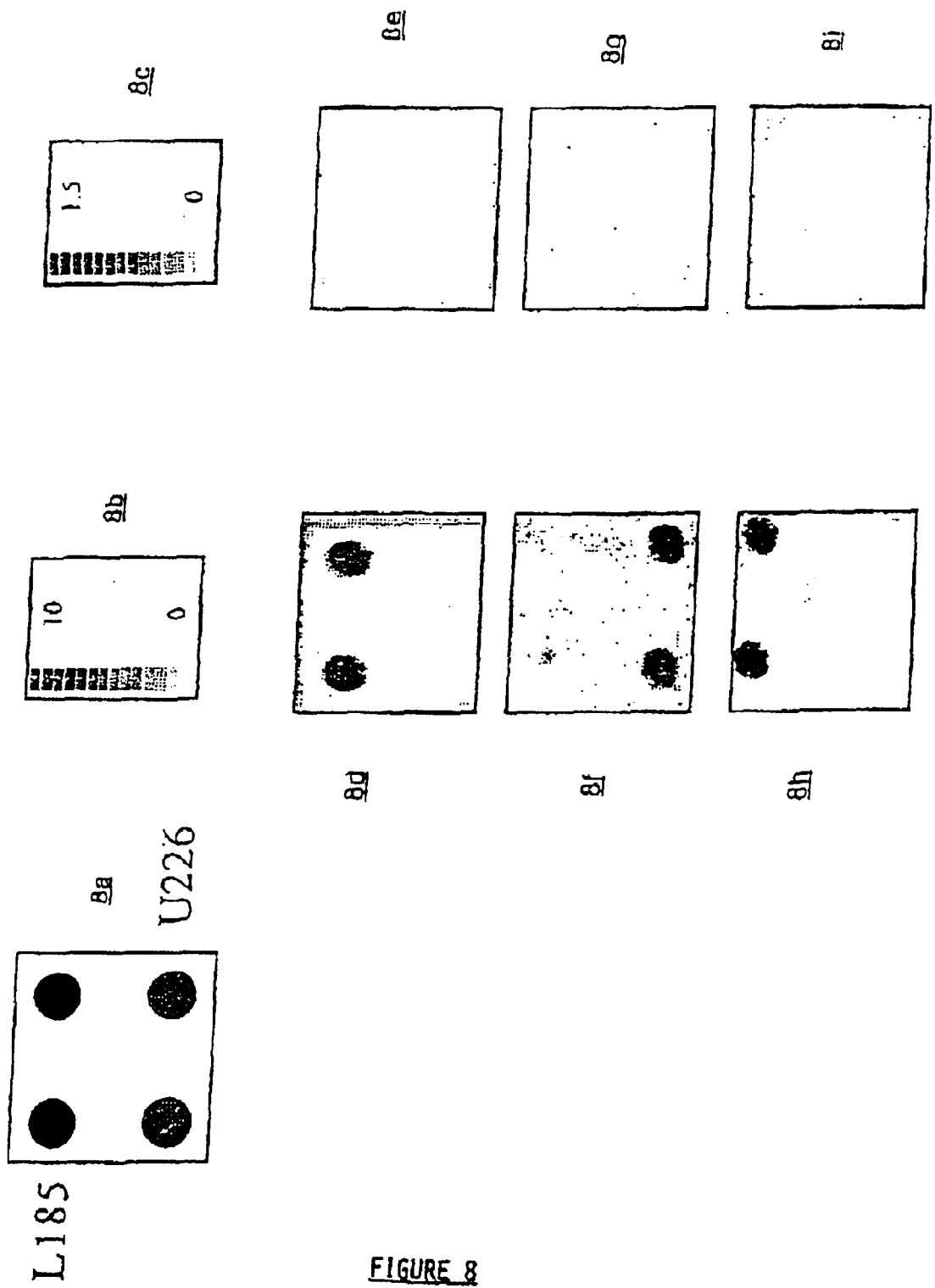
FIG. 8 represents successive experiments consisting of hybridization (FIGS. 8d, 8f and 8h) and of denaturation FIGS. 8e, 8g and 8i) using Au/Si/$SiO_2$ substrates modified with a monolayer of organosilicon compounds of formula (I) on which the oligonucleotides L185 and U226 have been synthesized FIG. 8a).

Oligonucleotides named L185 and U226 (sequence of 25 nucleotides) are synthesized at four points of this support, as illustrated in FIG. 8a. FIGS. 8b and 8c indicate, on a scale of 0 to 10 for FIG. 8b (serving as a scale for FIGS. 8d, 8f and 8h) and on a scale of 0 to 1.5 for FIG. 8c (serving as a scale for FIGS. 8e, 8g and 8i), the fluorescence intensities depicted on the support.

FIG. 8d represents the fluorescence intensity detected after having brought the support into contact with a solution of an oligonucleotide complementary to L185 comprising fluorescence labels, after having washed the support. The hybridization is carried out at 46° C. overnight in the presence of a TRIS buffer, pH 7.1, comprising 50 mM of NaCl. The concentration of the oligonucleotide L185 in the TRIS is 0.01 mg/ml. Each strand complementary to L185 carries a fluorescent group Cy3 at the 5' end. Hybridization of the complementary sequence with the sequence L185 is clearly observed. [f ] FIG. 8e corresponds to the support after denaturation: the complementary sequence is no longer detected.

FIG. 8f represents the fluorescence intensity detected after having brought the support into contact with a solution of an oligonucleotide complementary to U226 comprising fluorescence labels, after having washed the support, under the same conditions as indicated above with the respect to the L185 strand. Here again, hybridization of the complementary sequence with the sequence U226 is observed. FIG. 8g corresponds to the support after denaturation: the complementary sequence is no longer detected.

FIG. 8h represents the fluorescence intensity detected after having once again brought the support into contact with a solution of an oligonucleotide complementary to L185 comprising fluorescence labels, after having washed the support. Hybridization of the complementary sequence with the sequence L185 again occurs. FIG. 8i shows the absence of the complementary sequence after denaturation.

These experiments show that nucleic acids synthesized directly on a solid support modified with an organized self-assembled monolayer of organosilicon compounds of formula (I), this synthesis carried out in accordance with the method according to the present invention, can give rise to selective hybridization reactions with complementary sequences, the support being reusable in several successive cycles of hybridization and denaturation.

EXAMPLE 7

Immobilization of Presynthesized Nucleic Acids on a Solid Support Modified with an Organized Self-assembled Monolayer of Organosilicon Compounds of Formula (I)

1) Preparation of the Solid Support Modified with an Organized Self-assembled Monolayer The procedure is carried out as in example 5, with the difference that the organized self-assembled monolayer comprises the organosilicon compound of formula 16 prepared according to the protocol indicated in example 1. It is clearly understood that use may be made of any other organosilicon compound of formula (I) (or a mixture of organosilicon compounds comprising at least one organosilicon compound of formula (I)), said compound of formula (I) carrying a protected carboxylic acid function. The ends of the organosilicon compounds are converted to carboxylic acid groups by hydrolysis of the esters (for example under the action of triiodomethylsilane or of concentrated hydrochloric acid).

2) Immobilization of Nucleic Acids on this Support

The carboxylic acid functions of the support are activated with a solution of N-hydroxysuccinimide. The support thus activated is brought into contact with a solution of the nucleic acid to be immobilized (1 µg/µl in a 9/1 by volume acetonitrile/water mixture, in the presence of triethylamine), this nucleic acid carrying a spacer arm functionalized with an amine function. The reaction is carried out at ambient temperature, optionally until drying of the solution. The support is then washed with a TRIS buffer, pH 7.1. This operation makes it possible to block the acid functions which have not reacted via reaction with an amine (capping reaction).

As emerges from the above, the invention is in no way limited to its methods of implementation, preparation and application which have just been described more explicitly; on the contrary, it encompasses all the variants thereof which may occur to a person skilled in the art, without departing from the context or the scope of the present invention.

In particular, although only methods for synthesizing and immobilizing nucleic acids have been described, it is clearly understood that the methods according to the invention may also be applied to other biomolecules, in particular proteins; in which case, the method of synthesis according to the invention would comprise successive steps for grafting the basic units of these biomolecules onto the support (for example amino acids), the steps carried out being, nevertheless, the same as those described more precisely with respect to nucleic acids.

What is claimed is:

1. A solid support for synthesizing or immobilizing nucleic acids, wherein said solid support is modified with an organized self-assembled monolayer comprising at least one organosilicon compound corresponding to formula (I):

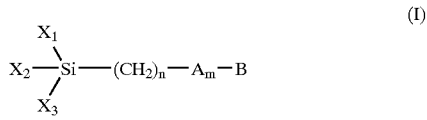

in which:
$X_1$, $X_2$ and $X_3$ represent chlorine atoms,
n is equal to 22,
A represents the group —O—$(CH_2$—$CH_2$—$O)_k$—$(CH_2)_i$— in which k is equal to 1 or to 3 and i is equal to 0,
m is equal to 1,
B represents a group —$COCH_3$.

2. The support as claimed in claim 1, characterized in that said solid support is selected from the group consisting of glasses, ceramics, metals and metalloids.

3. A solid support for synthesizing or immobilizing nucleic acids, wherein said solid support is modified with an organized self-assembled monolayer comprising at least one organosilicon compound corresponding to formula (I):

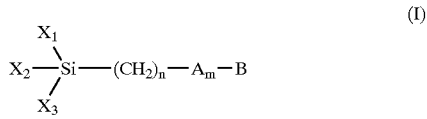

in which:
$X_1$, $X_2$ and $X_3$ represent chlorine atoms,
n is equal to 22,
A represents the group —O—$(CH_2$—$CH_2$—$O)_k$—$(CH_2)_i$— in which k is equal to 2 and i is equal to 1,
m is equal to 1,
B represents a group —$COOCH_3$.

4. A solid support for synthesizing or immobilizing nucleic acids, wherein said solid support is modified with an organized self-assembled monolayer comprising at least one organosilicon compound corresponding to formula (I):

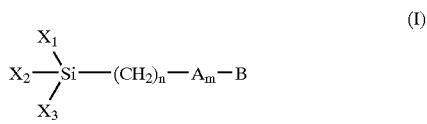

in which:
$X_1$, $X_2$ and $X_3$ represent chlorine atoms,
n is equal to 16, 22 or 27,
A represents the group —O—$(CH_2$—$CH_2$—$O)_k$—$(CH_2)_i$— in which k is between 0 and 100 and i represents an integer greater than or equal to 0,
m is equal to 0 and
B represents a group —$OCOCH_3$.

5. A solid support for synthesizing or immobilizing nucleic acids, wherein said solid support is modified with an organized self-assembled monolayer comprising at least one organosilicon compound corresponding to formula (I):

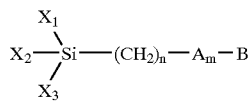
(I)

in which:

X₁, X₂ and X₃ represent chlorine atoms, n is equal to 21,

A represents the group —O—(CH₂—CH₂—O)$_k$— (CH₂)$_i$— in which k is between 0 and 100 and i represents an integer greater than or equal to 0, m is equal to 0 and B represents a group —COOCH₃.

6. The support as claimed in claim 1, wherein said support is for preparing DNA chips.

7. A method for synthesizing nucleic acids on a solid support, characterized in that said support is modified with an organized self-assembled monolayer comprising at least one organosilicon compound corresponding to formula (I) as defined in claim 1, and in that it comprises the following steps:
   a) preparing a solid support modified with an organized self-assembled monolayer comprising at least one organosilicon compounds corresponding to formula (I) as defined in claim 1, in which said organosilicon compounds have, at their end, a protected amine or hydroxyl function;
   b) optionally deprotecting the amine or hydroxyl function;
   c) covalently coupling, in a localized manner, a nucleotide to the modified solid support obtained in step a) or b);
   d) reiterating step c) at least once, with identical or different nucleotides.

8. The method as claimed in claim 7, characterized in that step a) is carried out via the following steps:
   i) removing the contaminants from the solid support and hydrating and/or hydroxylating its surface,
   j) introducing an organosilicon compound of general formula (I) as defined in claim 6, into a mixture of at least two solvents comprising at least one nonpolar hydrocarbon-based solvent, under an inert atmosphere, said compound having, at one end, a protected amine or hydroxyl function,
   k) silanizing the support obtained in step i) by immersion in the solution prepared in step j),
   l) optionally annealing the silanized support obtained in step k), carrying the self-assembled monolayer, at a temperature between 50 and 120° C., for a period of 5 minutes to overnight, and
   m) rinsing the modified support obtained in step k) or l), with a solvent.

9. The method as claimed in claim 7, characterized in that a step for grafting, to the end of said organosilicon compounds, spacer arms carrying terminal amine or hydroxyl functions is carried out after step a) or b) and before step c).

10. The method as claimed in claim 7, characterized in that the nucleotides coupled in step c) are protected and in that step d) is followed by a step of deprotection of the nucleic acid synthesized.

11. A method for immobilizing nucleic acids on a solid support, characterized in that said support is modified with an organized self-assembled monolayer comprising at least one organosilicon compounds corresponding to formula (I) as defined in claim 1, and in that it comprises the following steps:
   a) preparing a solid support modified with an organized self-assembled monolayer comprising at least one organosilicon compound corresponding to formula (I) as defined in claim 1, in which said organosilicon compounds have, at their end, a protected amine or carboxylic acid function;
   b) optionally deprotecting the amine or carboxylic acid function;
   c) optionally, when the modified solid support carries terminal carboxylic acid functions, activating these functions;
   d) bringing the modified solid support obtained in step a), b) or c) into contact with one or more solutions, applied locally, in one or more polar solvents, of the nucleic acid(s) to be immobilized, said nucleic acids carrying, at one of their ends, a spacer arm functionalized either with an amine function, when the modified solid support carries optionally protected terminal carboxylic acid functions, or with an activated carboxylic acid function, when the modified solid support carries optionally protected terminal amine functions; and
   e) washing the solid support on which said nucleic acids are immobilized.

12. The method as claimed in claim 11, characterized in that step a) is carried out via the following steps:
   i) removing the contaminants from the solid support and hydrating and/or hydroxylating its surface,
   j) introducing an organosilicon compound of general formula (I) as defined in claims 1, into a mixture of at least two solvents comprising at least one nonpolar hydrocarbon-based solvent, under an inert atmosphere, said compound having, at one end, a protected amine or carboxylic acid function,
   k) silanizing the support obtained in step i) by immersion in the solution prepared in step j), and
   l) optionally annealing the silanized support obtained in step k), carrying the self-assembled monolayer, at a temperature between 50 and 120° C., for a period of 5 minutes to overnight, and
   m) rinsing the modified support obtained in step k) or l), with a solvent.

13. The method as claimed in claim 11, characterized in that a step for grafting, to the end of said organosilicon compounds, spacer arms carrying terminal amine or carboxylic acid functions is carried out after step a) or b) and before step c).

14. A DNA chip, characterized in that it is obtained using the method as claimed in claim 11, in which said nucleic acids are DNAs.

15. The support as claimed in claim 3, characterized in that said solid support is selected from the group consisting of glasses, ceramics, metals and metalloids.

16. The support as claimed in claim 4, characterized in that said solid support is selected from the group consisting of glasses, ceramics, metals and metalloids.

17. The support as claimed in claim 5, characterized in that said solid support is selected from the group consisting of glasses, ceramics, metals and metalloids.

18. The support as claimed in claim 3, wherein said support is for preparing DNA chips.

19. The support as claimed in claim 4, wherein said support is for preparing DNA chips.

20. The support as claimed in claim 5, wherein said support is for preparing DNA chips.

21. A method for synthesizing nucleic acids on a solid support, characterized in that said support is modified with an organized self-assembled monolayer comprising at least one organosilicon compound corresponding to formula (I) as defined in claim 3, and in that it comprises the following steps:
   a) preparing a solid support modified with an organized self-assembled monolayer comprising at least one organosilicon compounds corresponding to formula (I) as defined in claim 3, in which said organosilicon compounds have, at their end, a protected amine or hydroxyl function;
   b) optionally deprotecting the amine or hydroxyl function;
   c) covalently coupling, in a localized manner, a nucleotide to the modified solid support obtained in step a) or b);
   d) reiterating step c) at least once, with identical or different nucleotides.

22. A method for synthesizing nucleic acids on a solid support, characterized in that said support is modified with an organized self-assembled monolayer comprising at least one organosilicon compound corresponding to formula (I) as defined in claim 4, and in that it comprises the following steps:
   a) preparing a solid support modified with an organized self-assembled monolayer comprising at least one organosilicon compounds corresponding to formula (I) as defined in claim 4, in which said organosilicon compounds have, at their end, a protected amine or hydroxyl function;
   b) optionally deprotecting the amine or hydroxyl function;
   c) covalently coupling, in a localized manner, a nucleotide to the modified solid support obtained in step a) or b);
   d) reiterating step c) at least once, with identical or different nucleotides.

23. A method for synthesizing nucleic acids on a solid support, characterized in that said support is modified with an organized self-assembled monolayer comprising at least one organosilicon compound corresponding to formula (I) as defined in claim 5, and in that it comprises the following steps:
   a) preparing a solid support modified with an organized self-assembled monolayer comprising at least one organosilicon compounds corresponding to formula (I) as defined in claim 5, in which said organosilicon compounds have, at their end, a protected amine or hydroxyl function;
   b) optionally deprotecting the amine or hydroxyl function;
   c) covalently coupling, in a localized manner, a nucleotide to the modified solid support obtained in step a) or b);
   d) reiterating step c) at least once, with identical or different nucleotides.

24. A method for immobilizing nucleic acids on a solid support, characterized in that said support is modified with an organized self-assembled monolayer comprising at least one organosilicon compounds corresponding to formula (I) as defined in claim 3, and in that it comprises the following steps:
   a) preparing a solid support modified with an organized self-assembled monolayer comprising at least one organosilicon compound corresponding to formula (I) as defined in claim 3, in which said organosilicon compounds have, at their end, a protected amine or carboxylic acid function;
   b) optionally deprotecting the amine or carboxylic acid function;
   c) optionally, when the modified solid support carries terminal carboxylic acid functions, activating these functions;
   d) bringing the modified solid support obtained in step a), b) or c) into contact with one or more solutions, applied locally, in one or more polar solvents, of the nucleic acid(s) to be immobilized, said nucleic acids carrying, at one of their ends, a spacer arm functionalized either with an amine function, when the modified solid support carries optionally protected terminal carboxylic acid functions, or with an activated carboxylic acid function, when the modified solid support carries optionally protected terminal amine functions; and
   e) washing the solid support on which said nucleic acids are immobilized.

25. A method for immobilizing nucleic acids on a solid support, characterized in that said support is modified with an organized self-assembled monolayer comprising at least one organosilicon compounds corresponding to formula (I) as defined in claim 4, and in that it comprises the following steps:
   a) preparing a solid support modified with an organized self-assembled monolayer comprising at least one organosilicon compound corresponding to formula (I) as defined in claim 8, in which said organosilicon compounds have, at their end, a protected amine or carboxylic acid function;
   b) optionally deprotecting the amine or carboxylic acid function;
   c) optionally, when the modified solid support carries terminal carboxylic acid functions, activating these functions;
   d) bringing the modified solid support obtained in step a), b) or c) into contact with one or more solutions, applied locally, in one or more polar solvents, of the nucleic acid(s) to be immobilized, said nucleic acids carrying, at one of their ends, a spacer arm functionalized either with an amine function, when the modified solid support carries optionally protected terminal carboxylic acid functions, or with an activated carboxylic acid function, when the modified solid support carries optionally protected terminal amine functions; and
   e) washing the solid support on which said nucleic acids are immobilized.

26. A method for immobilizing nucleic acids on a solid support, characterized in that said support is modified with an organized self-assembled monolayer comprising at least one organosilicon compounds corresponding to formula (I) as defined in claim 5, and in that it comprises the following steps:
   a) preparing a solid support modified with an organized self-assembled monolayer comprising at least one organosilicon compound corresponding to formula (I) as defined in claim 5, in which said organosilicon compounds have, at their end, a protected amine or carboxylic acid function;
   b) optionally deprotecting the amine or carboxylic acid function;
   c) optionally, when the modified solid support carries terminal carboxylic acid functions, activating these functions;

d) bringing the modified solid support obtained in step a), b) or c) into contact with one or more solutions, applied locally, in one or more polar solvents, of the nucleic acid(s) to be immobilized, said nucleic acids carrying, at one of their ends, a spacer arm functionalized either with an amine function, when the modified solid support carries optionally protected terminal carboxylic acid functions, or with an activated carboxylic acid function, when the modified solid support carries optionally protected terminal amine functions; and e) washing the solid support on which said nucleic acids are immobilized.

* * * * *